United States Patent
Blomström et al.

(10) Patent No.: US 12,042,367 B2
(45) Date of Patent: Jul. 23, 2024

(54) SANITARY ARTICLE HAVING ASSYMMETRICAL FASTENING WINGS

(71) Applicant: Essity Hygiene and Health Aktiebolag, Gothenburg (SE)

(72) Inventors: Philip Blomström, Gothenburg (SE); Charlotte Pollard, Asa (SE)

(73) Assignee: ESSITY HYGIENE AND HEALTH AKTIEBOLAG, Gothenburg (SE)

(*) Notice: Subject to any disclaimer, the term of this patent is extended or adjusted under 35 U.S.C. 154(b) by 0 days.

(21) Appl. No.: 17/783,943

(22) PCT Filed: Dec. 13, 2019

(86) PCT No.: PCT/SE2019/051282
§ 371 (c)(1),
(2) Date: Jun. 9, 2022

(87) PCT Pub. No.: WO2021/118422
PCT Pub. Date: Jun. 17, 2021

(65) Prior Publication Data
US 2023/0240914 A1 Aug. 3, 2023

(51) Int. Cl.
A61F 13/56 (2006.01)
A61F 13/15 (2006.01)
(Continued)

(52) U.S. Cl.
CPC .... A61F 13/5616 (2013.01); A61F 13/47245 (2013.01); A61F 13/5514 (2013.01);
(Continued)

(58) Field of Classification Search
CPC .......... A61F 13/56; A61F 13/58; A61F 13/60; A61F 13/5605
(Continued)

(56) References Cited

U.S. PATENT DOCUMENTS 3,595,237 A * 7/1971 Sargent ............... A61F 13/5611
604/366
4,500,316 A 2/1985 Damico
(Continued)

FOREIGN PATENT DOCUMENTS

CA 2339513 A1 9/2001
CN 1056048 A 11/1991
(Continued)

OTHER PUBLICATIONS

Malaysian Application No. PI2020000003; Malaysian Search Report dated May 27, 2022; 2 pages.
(Continued)

*Primary Examiner* — Michele Kidwell
(74) *Attorney, Agent, or Firm* — CANTOR COLBURN LLP (57) ABSTRACT

The present disclosure relates to a sanitary article (1), such as a sanitary napkin or a pantiliner. The sanitary article (1) has a first fastening wing (9) extending at a first longitudinal side edge (5) and a second fastening wing (10) extending at a second longitudinal side edge (6), the first fastening wing (9) having a first wing maximum width ($W_{f1max}$) and the second fastening wing (10) having a second wing maximum width ($W_{f2max}$). The first fastening wing (9) comprises a first adhesive region (12) on a garment facing side thereof and the second fastening wing (10) comprises a second adhesive region (13) on a garment facing side thereof, the first and the second adhesive regions (12,13) having a respective adhesive region maximum width ($w_{a1max}$, $w_{a2max}$). The first and the second adhesive region (12,13) are covered with a common release paper (14,140), the common release paper (14,140) having a width ($w_t$), as seen in the transverse direction. The first and the second fastening wings (9,10) are arranged in a folded configuration onto the topsheet (2) in a non-overlapping manner. The first and second fastening (Continued)

wings (9,10) are asymmetrical with respect to any transverse and longitudinal axis and the width of the release paper ($w_r$) is not more than 7 mm greater than the sum of the first and the second adhesive region maximum widths, $w_{a1max} + w_{a2max}$.

15 Claims, 4 Drawing Sheets

(51) Int. Cl.
    *A61F 13/47*     (2006.01)
    *A61F 13/472*    (2006.01)
    *A61F 13/551*    (2006.01)
(52) U.S. Cl.
    CPC .............. *A61F 2013/15365* (2013.01); *A61F 2013/4708* (2013.01)
(58) Field of Classification Search
    USPC .................................................... 604/385.04
    See application file for complete search history.

(56) References Cited

U.S. PATENT DOCUMENTS

| | | | |
|---|---|---|---|
| 5,201,727 A | | 4/1993 | Nakanishi et al. |
| 5,401,268 A | * | 3/1995 | Rodier .............. A61F 13/15577 |
| | | | 604/383 |
| 5,429,630 A | | 7/1995 | Beal et al. |
| 5,733,274 A | | 3/1998 | Osborn, III |
| 6,013,062 A | * | 1/2000 | Dilnik ................. A61F 13/5616 |
| | | | 604/386 |
| 6,293,932 B1 | | 9/2001 | Balzar et al. |
| 6,447,495 B1 | * | 9/2002 | Luizzi ................... A61F 13/476 |
| | | | 604/385.03 |
| 6,746,435 B1 | | 6/2004 | Van Tilburg |
| 8,986,273 B2 | * | 3/2015 | Mercer ............... A61F 13/5616 |
| | | | 604/385.03 |
| 9,775,752 B2 | * | 10/2017 | Park .................... A61F 13/5514 |
| 10,258,513 B2 | | 4/2019 | Kuramochi |
| 11,000,431 B2 | * | 5/2021 | Blomström ....... A61F 13/15756 |
| 11,065,161 B2 | | 7/2021 | Blomström |
| 11,246,770 B2 | | 2/2022 | Vohwinkel et al. |
| 2003/0208177 A1 | | 11/2003 | D Alessio et al. |
| 2004/0138636 A1 | * | 7/2004 | Cardin .............. A61F 13/47245 |
| | | | 604/385.04 |
| 2005/0283131 A1 | | 12/2005 | Zander et al. |
| 2006/0271003 A1 | * | 11/2006 | Loescher ................. A61F 13/58 |
| | | | 604/372 |
| 2012/0109093 A1 | * | 5/2012 | Wilson .............. A61F 13/15756 |
| | | | 604/385.05 |
| 2012/0259306 A1 | * | 10/2012 | Petersen ............. A61F 13/5605 |
| | | | 604/385.05 |
| 2012/0316533 A1 | * | 12/2012 | Norimoto ........... A61F 13/5514 |
| | | | 604/385.02 |
| 2013/0123731 A1 | | 5/2013 | Mercer et al. |
| 2013/0310784 A1 | | 11/2013 | Bryant et al. |
| 2018/0325750 A1 | * | 11/2018 | Vohwinkel ............ A61F 13/476 |
| 2018/0325751 A1 | | 11/2018 | Vohwinkel et al. |
| 2018/0325753 A1 | | 11/2018 | Vohwinkel |
| 2018/0325754 A1 | | 11/2018 | Vohwinkel et al. |
| 2020/0129347 A1 | | 4/2020 | Blomström et al. |
| 2020/0155364 A1 | | 5/2020 | Rönnberg et al. |
| 2020/0368083 A1 | | 11/2020 | Rönnberg et al. |
| 2023/0022804 A1 | | 1/2023 | Pollard |

FOREIGN PATENT DOCUMENTS

| | | | | |
|---|---|---|---|---|
| CN | 1073090 | A | 6/1993 | |
| CN | 1203520 | A | 12/1998 | |
| CN | 1312060 | A | 9/2001 | |
| CN | 1315168 | A | 10/2001 | |
| CN | 101878011 | A | 11/2010 | |
| CN | 101999964 | A | 4/2011 | |
| CN | 203915242 | U | 11/2014 | |
| CN | 204501249 | U | 7/2015 | |
| CN | 105188626 | A | 12/2015 | |
| CN | 105455962 | A | 4/2016 | |
| CN | 106488760 | A | 3/2017 | |
| CN | 206102848 | A | 4/2017 | |
| CN | 106794099 | A | 5/2017 | |
| CN | 107427402 | A | 12/2017 | |
| CO | 5160278 | A1 | 5/2002 | |
| EP | 0471385 | A1 | 2/1992 | |
| EP | 0 471 385 | * | 2/1999 | ............. A61F 13/58 |
| EP | 0 983 760 | * | 3/2000 | ............. A61F 13/58 |
| EP | 1138294 | A1 | 10/2001 | |
| EP | 1208823 | A1 | 5/2002 | |
| ES | 2230013 | T3 | 5/2005 | |
| JP | H05506799 | A | 10/1993 | |
| JP | H0586322 | U | 11/1993 | |
| JP | 2009213719 | A | 9/2009 | |
| JP | 2010227241 | A | 10/2010 | |
| JP | 2011045608 | A | 3/2011 | |
| JP | 2013220225 | A | 10/2013 | |
| JP | 2014150878 | A | 8/2014 | |
| JP | 2016104089 | A | 6/2016 | |
| KR | 20050008509 | A | 1/2005 | |
| RU | 2277891 | C2 | 6/2006 | |
| WO | 9116873 | A1 | 11/1991 | |
| WO | 9855063 | A1 | 12/1998 | |
| WO | 0021477 | A1 | 4/2000 | |
| WO | 0172254 | A2 | 10/2001 | |
| WO | 2010110270 | A1 | 9/2010 | |
| WO | 2013094779 | A1 | 6/2013 | |
| WO | 2016068957 | A1 | 5/2016 | |
| WO | 2019007527 | A1 | 1/2019 | |
| WO | 2019007529 | A1 | 1/2019 | |
| WO | 2019008090 | A1 | 1/2019 | |
| WO | 2019008091 | A1 | 1/2019 | |
| WO | 2019112641 | A1 | 6/2019 | |

OTHER PUBLICATIONS

Chinese Application No. 201980102566.6; Office Action dated Aug. 3, 2022; 14 pages.
Chinese Application No. 201980102571.7; Office Action dated Aug. 8, 2022; 19 pages.
Japanese Patent Office, Office Action issued in JP 2020-500129 dated Mar. 31, 2021 with English translation, 18 pages.
Japanese Patent Office, Office Action issued in JP Application No. 2020-500068, dated Feb. 2, 2021 with partial English Translation (14 pages).
National Intellectual Property Administration (CNIPA) of the People's Republic of China, First Office Action issued in CN Application No. 20170092879.9, dated Mar. 17, 2021 with English translation, 24 pages.
National Intellectual Property Administration (CNIPA) of the People's Republic of China, First Office Action, dated Apr. 20, 2020 and English Translation (13 pages).
Russian Patent Office, Decision to Grant issued in RU Application No. 219139870/03(078379), dated Jun. 25, 2020 with English Translation (22 pages).
Australian Government, IP Australia, Office Action issued in AU Application No. 2017422549, dated Apr. 21, 2020 (4 pages).
Colombian Patent Office, Office Action issued in CO application No. NC2020/0000068 dated Jul. 16, 2021 with English explanation of rejections/relevance from local counsel (11 pages).
Colombian Patent Office, Office Action issued in CO application No. NC2020/0000068 dated Nov. 30, 2021 (10 pages).
International Preliminary Report on Patentability for International Application No. PCT/EP2017/067068, dated Oct. 25, 2019, 18 pages.
International Preliminary Report on Patentability for International Application No. PCT/EP2017/067071, dated Oct. 25, 2019, 21 pages.
International Preliminary Report on Patentability for International Application No. PCT/EP2018/068232, dated Oct. 23, 2019, 21 pages.

(56) References Cited

OTHER PUBLICATIONS

International Preliminary Report on Patentability for International Application No. PCT/EP2018/068233, dated Oct. 21, 2019, 16 pages.
International Search Report and Written Opinion for International Application No. PCT/EP2017/067068, dated Jan. 8, 2018, 15 pages.
International Search Report and Written Opinion for International Application No. PCT/EP2017/067071, dated Jan. 8, 2018, 20 pages.
International Search Report and Written Opinion for International Application No. PCT/EP2018/068232, dated Aug. 16, 2018, 17 pages.
International Search Report and Written Opinion for International Application No. PCT/EP2018/068233, dated Aug. 17, 2018, 17 pages.
International Serach Report & Written Opinion for International Application No. PCT/SE2019/051281; International Filing Date: Dec. 13, 2019; Date of Mailing: Jul. 20, 2020; 15 pages.
International Serach Report & Written Opinion for International Application No. PCT/SE2019/051282; International Filing Date: Dec. 13, 2019; Date of Mailing: Jul. 20, 2020; 13 pages.
Japanese Patent Office, Office Action issued in JP 2020-500043 dated Mar. 31, 2021 with English translation, 17 pages.
Russian Patent Office, Decision to Grant issued in RU application No. 2019139865/(078371), dated Jul. 7, 2020 with English translation (21 pages).
National Intellectual Property Administration (CNIPA) of the People's Republic of China, Office Action issued in CN 201780092880.1 dated Mar. 29, 2021 with English Translation, 20 pages.
Japanese Patent Office, Office Action issued in JP Application No. 2020-500117, dated Feb. 1, 2021 with partial English Translation, 13 pages.
U.S. Final Office Action for U.S. Appl. No. 16/626,039; Application Filing Date Dec. 23, 2019; Report Mail Date Dec. 12, 2023 (29 Pages).
U.S. Final Office Action for U.S. Appl. No. 16/626,672; Application Filing Date Dec. 26, 2019; Report Mail Date Nov. 20, 2023 (30 Pages).
Mexican Application Office Action for Mexican Application No. MX/a/2019/015545; Report Mail Date Apr. 17, 2023 (5 Pages; with English translation).
Extended European Search Report for European Application No. 19955481.7; Report Mail Date Jun. 30, 2023 (5 Pages).
Merriam-Webster Dictionary, "Upside Down Definition & Meaning" https://www.merriam-webster.com/dictionary/upside%down (Year 2023).
U.S. Office Action for U.S. Appl. No. 16/626,039; Application Filing Date Dec. 23, 2019; Report Mail Date Aug. 3, 2023 (pp. 1-19).
U.S. Office Action for U.S. Appl. No. 16/626,672; Application Filing Date Dec. 26, 2019; Report Mail Date Jul. 27, 2023 (pp. 1-21).
Office Action issued in Colombian Application No. NC2022/0008157 dated May 8, 2024.

\* cited by examiner

SANITARY ARTICLE HAVING ASSYMMETRICAL FASTENING WINGS

CROSS REFERENCE TO RELATED APPLICATIONS

This application is a National Stage application of PCT/SE2019/051282, filed Dec. 13, 2019, which is incorporated by reference in its entirety herein.

TECHNICAL FIELD

The present disclosure pertains to a sanitary article such as a sanitary napkin or a pantiliner. In particular, this disclosure pertains to a sanitary article having asymmetrical fastening wings, the fastening wings being folded on top of the sanitary article and provided with a fastening wing release paper.

BACKGROUND

A sanitary article of the kind to which this disclosure relates includes an absorbent pad arranged between a topsheet and a backsheet, it further includes so-called fastening wings provided with adhesive regions for fastening of the wings in a user undergarment. When using a sanitary article, the article should be designed to be comfortable to wear for the user and it should provide a high level of protection for the user undergarment and clothing. When wearing the sanitary article, the user often moves around which may cause the sanitary article to move as well. This may result in incorrect positioning of the sanitary article and undesired wrinkling and folding of the sanitary article, which may negatively affect comfort, absorption and protection of the user garments. To secure that the sanitary article remains in place, the size and width of the fastening wings may be increased.

When packaging sanitary articles, the fastening wings are conventionally folded on top of the topsheet of the sanitary article. Adhesive regions provided on the fastening wings are protected by a release paper covering the adhesive regions and keeping the fastening wings in place during manufacturing, storage and handling of the sanitary article.

In the area of sanitary articles there is a need and desire to reduce the environmental impact of sanitary articles, both in the choice of material, manufacturing methods and with respect to the amount of material used for each sanitary article. A very large number of sanitary articles are constantly being produced and every saving for each article represents a large total saving.

It is an object of the present invention to reduce the environmental impact of sanitary articles while yet providing a comfortable, secure and hygienic sanitary article.

SUMMARY

One or more of the above objects is achieved with a sanitary article in accordance with claim 1.

Further advantages and advantageous features of the invention are disclosed in the following description and in the dependent claims A sanitary article, such as a sanitary napkin or a pantiliner, according to the present disclosure comprises a topsheet, a backsheet and an absorbent core arranged between the topsheet and the backsheet. The sanitary article extends in a longitudinal direction and in a transverse direction. The sanitary article has a first and a second longitudinal side edge, a front edge and a rear edge. The absorbent core has a first and a second longitudinal core side edge, a front core edge and a rear core edge. The sanitary article has a first fastening wing extending outboard at the first longitudinal side edge and a second fastening wing extending outboard at the second longitudinal side edge. The first and the second fastening wings are asymmetrical with respect to any transverse axis extending in the transverse direction of the sanitary article and with respect to each other as seen along any longitudinal axis extending in the longitudinal direction of the sanitary article. The first fastening wing has a first wing maximum width and the second fastening wing has a second wing maximum width. The wing maximum widths being measured from the respective first and second longitudinal core side edge and at the widest section of the respective fastening wing, as seen in the transverse direction, the first fastening wing comprising a first adhesive region on a garment facing side thereof and the second fastening wing comprising a second adhesive region on a garment facing side thereof. The first adhesive region has a first adhesive region maximum width and the second adhesive regions has a second adhesive region maximum width, the adhesive region maximum widths being measured at the widest section of the respective adhesive region, as seen in the transverse direction. The first and the second adhesive regions are covered with a common release paper, the common release paper having a width, as seen in the transverse direction. The first and the second fastening wings are arranged in a folded configuration onto the topsheet in a non-overlapping manner. The width of the release paper is not more than 7 mm greater than the sum of the first and the second adhesive region maximum widths.

The first and second fastening wings are asymmetrical with respect to any transverse axis and are thus asymmetrical with respect to a fastening wing transverse centerline. The first and second fastening wings are also asymmetrical with respect to a sanitary article longitudinal centerline.

If the release paper has a varying width, the maximum width is intended herein.

The fastening of a sanitary napkin to an undergarment by means of fastening wings may be improved by means of larger fastening wings having a greater width. During manufacturing, the fastening wings are folded on top of the topsheet, the fastening wings are subsequently provided with adhesive on a garment facing side thereof and the adhesive zones may be covered with a common release paper, i.e. one single release paper, extending over the fastening wings in the transverse direction. A fastening wing adhesive region is conventionally provided over a rectangular area arranged with a certain distance, such as for example from 5 mm to 10 mm, from the edge of the fastening wing. The fastening wings may furthermore be folded such that the edges of the respective fastening wing are facing each other and are arranged with a certain distance from each other. This means that the width of the common release paper is at least the sum of the width of the first and second adhesive region, the distance between the fastening wings and the distance between the most proximal inner edge of the respective adhesive region, as measured when the fastening wings are in a folded configuration on the topsheet.

By giving the fastening wings an asymmetrical shape according to the present disclosure and by arranging the fastening wings such that the widest section of the fastening wings are not facing each other, as seen in the transverse direction, it has been found by the present inventors that the amount of release paper covering the adhesive regions on the fastening wings may be reduced.

Each of the fastening wings may thus extend over a longitudinal centerline of the sanitary article when arranged in the folded configuration without the fastening wings overlapping each other.

The width of the release paper may be maximum 4 mm greater than the sum of the first and the second adhesive region maximum widths.

The width of the release paper may be maximum 2 mm greater than the sum of the first and the second adhesive region maximum widths.

The width of the release paper may be maximum 1 mm greater than the sum of the first and the second adhesive region maximum widths.

The sum of the first and the second adhesive region maximum widths may be equal to or greater than the width of the release paper.

As the fastening wings have an asymmetrical shape according to the present disclosure and by arranging the fastening wings such that the widest section of the fastening wings are displaced with respect to each other and thereby are not facing each other, it has been found by the present inventors that the width of the release paper covering the adhesive regions on the fastening wings may be equal to or smaller than the sum of the first and the second adhesive region maximum widths. Either the first and second adhesive regions may be arranged in parallel as seen in the longitudinal direction or they may each have an adhesive region wider section and an adhesive region narrower section, wherein the adhesive region wider section of the first fastening wing faces the adhesive region narrower section of the second fastening wing or vice versa. The first adhesive region and/or the second adhesive region may each include multiple adhesive zones, e.g. two or more rectangular adhesive zones. The two or more rectangular adhesive zones in each adhesive region may have a first width and a second width, as seen in the transverse direction of the sanitary article, wherein the first width is greater than the second width.

The sum of the first and the second adhesive region maximum widths may be at least 2 mm greater than that the width of the release paper.

The sum of the first and the second wing maximum widths may be greater than a width of the absorbent core as measured at a sanitary article transverse centerline.

A width of the first fastening wing may continuously increase over at least 50% of the first fastening wing, as seen in the longitudinal direction of the sanitary article, from the rear portion and towards the front portion of the sanitary article, optionally a width of the first fastening wing may continuously increase over at least 75% of the first fastening wing, as seen in the longitudinal direction.

A width of the second fastening wing may continuously increase over at least 50% of the second fastening wing, as seen in the longitudinal direction, from the front portion and towards the rear portion of the sanitary article. The width of the second fastening wing may continuously increase over at least 75% of the second fastening wing from the front portion and towards the rear portion of the sanitary article The absorbent core may be an essentially rectangular core having a width not varying more than ±20 mm, or optionally ±10 mm, along a length of the absorbent core, the length extending in the longitudinal direction of the sanitary article. Such core configuration allows folding of the fastening wings close to the respective longitudinal side edges. This has the advantage of a reduced size of the sanitary article during transport and storage. This also enables the first and second fastening wing to be arranged closer together when being in a folded configuration and may thus both enable a reduced size release paper and a reduced sized folded sanitary article.

The first and second wings may be folded with a maximum distance of 5 mm between a respective longitudinal fold line of the first and second fastening wing and the first and the second longitudinal core edges.

The first and second wings may be folded directly at and around the first and second longitudinal core edges.

A length of the release paper may be less than a combined total length of the first and the second adhesive regions. The length being measured in the longitudinal direction of the sanitary article when the release paper has been applied to the adhesive regions of the fastening wings. The length being the maximum length of the respective adhesive region. The length of the release paper may be maximum 75% of the combined total length of the first and the second adhesive regions, or maximum 50% of the combined total length of the first and the second adhesive regions.

If the adhesive regions are constituted by separate zones, the length of the adhesive region is measured between the frontmost to the rearmost edge of the adhesive region and in the longitudinal direction.

The first fastening wing may have a first fastening wing edge section and the second fastening wing may have a second fastening wing edge section. When the fastening wings are folded onto the topsheet of the sanitary article, the first and the second fastening wing edge sections are arranged opposite and adjacent each other, a distance between the first and the second fastening wing edge sections may be 0 mm to 25 mm, optionally the distance between the first and the second fastening wing edge sections may be 0 mm to 10 mm, or 0 mm to 7 mm, optionally 0 mm to 4 mm. The first fastening wing edge section and the second fastening wing edge section may each have a length of from 10 mm or more along the first and the second fastening wing lateral edge. The first fastening wing edge section and the second fastening wing edge section may each have a length of from 15 mm to about 80 mm, as measured along a respective edge of the first and second fastening wing.

The first and/or the second adhesive regions may each have a non-rectangular shape. The first and the second adhesive regions may each have a respective portion with a greater width and a respective portion with a smaller width. The first adhesive region and/or the second adhesive region may each include multiple adhesive zones, e.g. two or more rectangular adhesive zones. The multiple adhesive zones may be separate zones or may be connected to form one continuous adhesive region. The two or more rectangular adhesive zones in each adhesive region may have a first width and a second width, as seen in the transverse direction of the sanitary article, wherein the first width is greater than the second width. The first adhesive region and the second adhesive region may be provided on the first and second fastening wings such that, when the fastening wings are folded on top of the topsheet, an adhesive zone with a first width on the first fastening wing is facing an adhesive zone with the second width on the second fastening wing and an adhesive zone with the second width on the first fastening wing is facing an adhesive zone with the first width on the second fastening wing The first and second adhesive region may also have a tapered shape.

If the adhesive regions are constituted by separate zones, the width of the adhesive region is measured between the innermost to the outermost edge of the adhesive region and in the transverse direction.

The first and the second fastening wing may be symmetrically disposed with respect to each other along a diagonal axis extending in a direction, in the plane of the sanitary article, and with an angle within the range of from 10° to 65°, such as within the range of from 30° to 55°, with respect to the longitudinal centerline of the sanitary article. Hence, the first and the second fastening wings may be mirror-images of each other if being turned 180° and may be arranged to extend outboard at the respective first and second longitudinal side edge at a respective location along the respective first and second longitudinal side edge such that they are symmetrically disposed with respect to each other.

When the fastening wings are symmetrically disposed with respect to each other along a diagonal axis extending in a direction, in the plane of the sanitary article and with an angle within the range of from 10° to 65° with respect to the longitudinal centerline of the sanitary article, and asymmetric with respect to any transverse axis extending in the transverse direction of the sanitary article, such as for example with respect to a transverse centerline of the fastening wings, and asymmetrically with respect to each other as seen along any longitudinal axis extending in the longitudinal direction of the sanitary article, the symmetry of the fastening wings may promote increased coverage of the release paper over the adhesive regions of the fastening wings despite the reduced size of the release paper. Such configuration of the fastening wings may also ensure an improved fastening symmetry of the fastening wings with fastening wings having an increased width without overlapping each other upon fastening of the fastening wings to the undergarment. This has been seen to provide enhanced fastening by preventing twisting and turning of the sanitary article in the undergarments, which could otherwise lead to leakage and be uncomfortable to the wearer.

The release paper may have the shape of a rhombus or parallelogram, having release paper first and second longitudinal edges and release paper first and second transverse edges. The release paper is provided over the first and second adhesive regions on the first and the second fastening wings and is arranged such that the release paper first and second longitudinal edges extend in the longitudinal direction of the sanitary article and the release paper first and second transverse edges are inclined with respect to the transverse direction of the sanitary article. Such configuration of the release paper may promote increased coverage of the release paper over the adhesive regions of the fastening wings despite the reduced width of the release paper.

The term "sanitary article" refers to products that are placed against the skin of the wearer to absorb and contain body exudates, like menstrual fluid and urine. The disclosure mainly refers to disposable sanitary articles, which means articles that are not intended to be laundered or otherwise restored or reused as a sanitary article. Examples of disposable sanitary articles include feminine sanitary napkins, pantiliners and the like.

The sanitary article includes outwardly projecting fastening wings made of a flexible material and extending outwardly on a respective side of the absorbent core. The first fastening wing extends at the first longitudinal side edge from a first front inflection point to a first rear inflection point and the second fastening wing extends at the second longitudinal side edge from a second front inflection point to a second rear inflection point, the inflection points being the point at which a fastening wing curvature occurs and thus a fastening wing point of beginning or end.

The adhesive regions on the fastening wing may for example comprise a pressure sensitive adhesive or another for the purpose suitable adhesive.

The topsheet may include or consist of fibrous nonwoven layer(s) being spunbonded, meltblown, carded, hydroentangled, wetlaid. Suitable nonwoven materials can be composed of natural fibers, such as woodpulp or cotton fibers, synthetic thermoplastic fibers, such as polyolefins, polyesters, polyamides and blends and combinations thereof or from mixtures of natural and synthetic fibers. The materials suited as topsheet material should be soft and non-irritating to the skin and be readily penetrated by body fluid, such as menstrual fluid and urine.

The absorbent core may be of any conventional kind. Examples on commonly occurring absorbent materials are cellulosic fluff pulp, tissue layers, highly absorbent polymers (so-called superabsorbents), absorbent foam materials, absorbent nonwoven materials or the like. It is common to combine cellulosic fluff pulp with superabsorbents in an absorbent structure. It is also common to have absorbent structures comprising layers of different material with different properties with respect to liquid acquisition capacity, liquid distribution capacity and storage capacity.

The backsheet may consist of a thin plastic film, e.g. a polyethylene or polypropylene film, a nonwoven material coated with a liquid impervious material, a hydrophobic nonwoven, which resist liquid penetration. Laminates of plastic films and nonwoven materials may also be used. The backsheet material can be breathable to allow vapor to escape from the absorbent structure, while still preventing liquids from passing through the backsheet material.

The sanitary article according to the present disclosure may be provided with an adhesive, such as a pressure-sensitive adhesive on the backsheet. The elongated wrapping sheet may be releasably adhered to the adhesive-bearing backsheet of the sanitary article. The wrapping sheet may be coated with material which enables the release of the wrapping sheet, such as silicone, so that the wrapping sheet may be peeled away from the adhesive-bearing backsheet of the sanitary article and so that the sanitary article may be attached to an undergarment. The adhesive-bearing region of the backsheet may also be covered with a release paper. The release paper may be attached to the wrapping sheet, for example with a permanent attachment, such that the sanitary article is attached to the wrapping sheet via the release paper.

BRIEF DESCRIPTION OF THE DRAWINGS

The present invention will be further explained hereinafter by means of non-limiting examples and with reference to the appended drawings wherein.

DETAILED DESCRIPTION

The invention will be described more closely below by reference to an exemplary embodiment. The invention may however be embodied in many different forms and should not be construed as limited to the embodiments set forth in the drawings and the description thereto.

Figure 1:
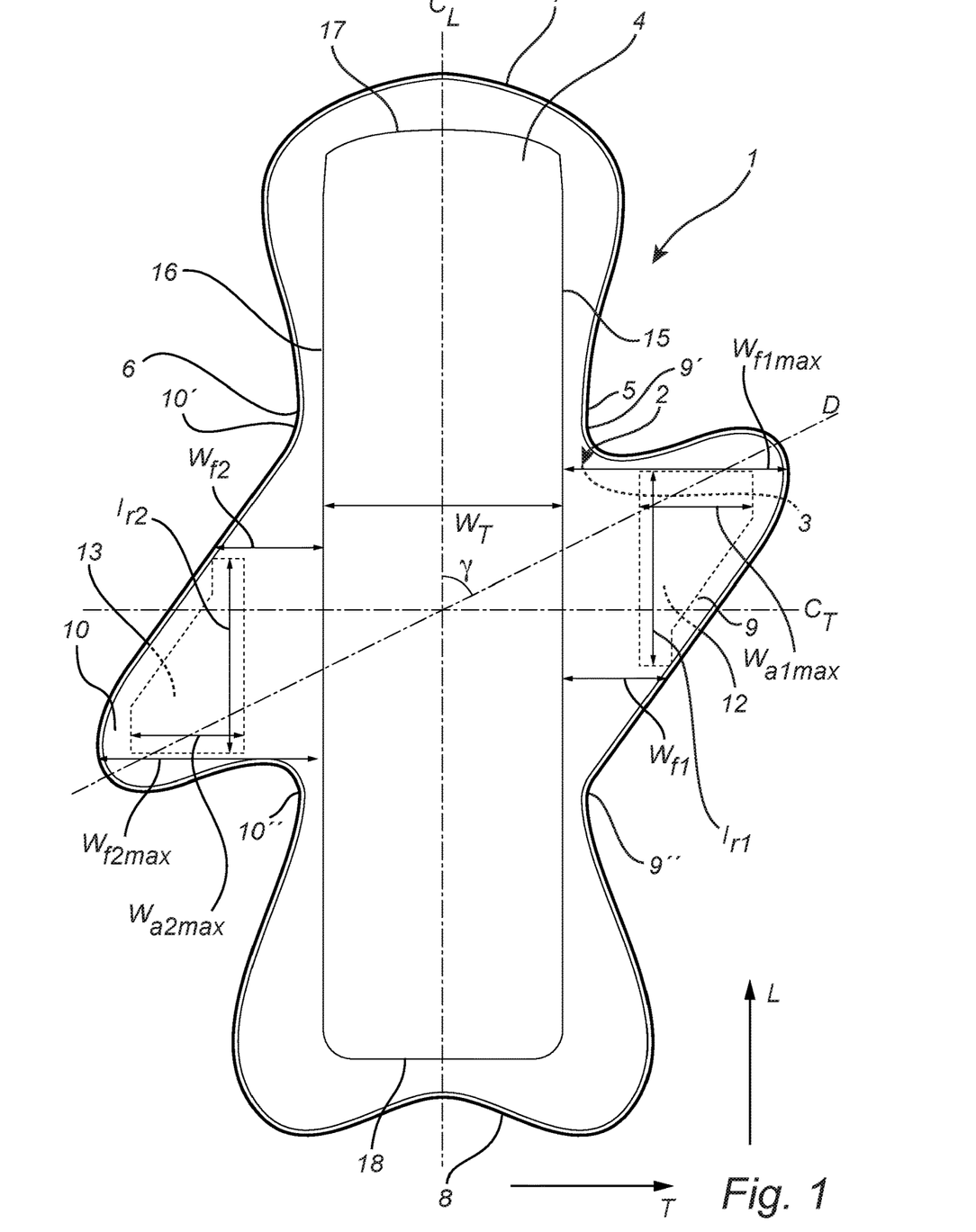
FIG. 1 illustrates a sanitary article, prior to folding of the sanitary article according to the present invention.

FIG. 1 illustrates a sanitary article 1 comprising a topsheet 2, a backsheet 3 and an absorbent core 4 arranged between the topsheet 2 and the backsheet 3. The sanitary article 1 extends in a longitudinal direction L and in a transverse direction T. A longitudinal centerline $C_L$ of the sanitary article 1 extends in the longitudinal direction L. A transverse centerline $C_T$ of the sanitary article 1 extends in the transverse direction T.

The sanitary article 1 has a first longitudinal side edge 5 and a second longitudinal side edge 6, a front edge 7 and a rear edge 8. The absorbent core 4 comprises a first longitudinal core side edge 15, a second longitudinal core side edge 16, a front core edge 17 and a rear core edge 18.

In this figure, the absorbent core 4 is an essentially rectangular core 4 having a width not varying more than ±10 mm along a longitudinal length of the absorbent core 4. However, the absorbent core may also have a varying width, with for example a wider front and/or rear portion and a narrower waist portion.

The sanitary article 1 has a first fastening wing 9 extending outboard at the first longitudinal side edge 5 and a second fastening wing 10 extending outboard at the second longitudinal side edge 6. The first fastening wing 9 extends at the first longitudinal side edge 5 from a first front inflection point 9' to a first rear inflection point 9" and the second fastening wing 10 extends at the second longitudinal side edge 6 from a second front inflection point 10' to a second rear inflection point 10", the inflection points being the point at which a fastening wing curvature occurs and thus a fastening wing point of beginning or end.

The first fastening wing 9 has a first wing maximum width $w_{f1max}$ and the second fastening wing 10 has a second wing maximum width $w_{f2max}$, the first and the second wing maximum width $w_{f1max}$, $w_{f2max}$ being measured from the respective first and second longitudinal core side edge and at the widest section of the respective fastening wing 9, 10 as seen in the transverse direction T. The first and second fastening wings 9, 10 are asymmetrical with respect to any transverse axis extending in the transverse direction T and with respect to each other as seen along any longitudinal axis extending in the longitudinal direction, such as with respect to the longitudinal centerline $C_L$ of the sanitary article 1. The first and the second fastening wings 9, 10 are furthermore symmetrically disposed with respect to each other along a diagonal axis D extending in a direction, in the plane of the sanitary article and with an angle α within the range of from 10° to 65° with respect to the longitudinal centerline $C_L$ of the sanitary article 1, such as for example within the range of from 30° to 55°. As may be seen in FIG. 1, the first and the second fastening wings 9, 10 may be mirror-images of each other if being turned 180° and may arranged to extend outboard at the respective first and second longitudinal side edge 5, 6 at a respective location along the respective first and second longitudinal side edge 5, 6 such that they are symmetrically disposed with respect to each other.

The first fastening wing 9 has a width $w_{f1}$ continuously increasing over at least 75% of the first fastening wing 9, as seen from the rear edge 8 and towards the front edge 7 of the sanitary article 1. The second fastening wing 10 has a width $w_{f2}$ continuously increasing over at least 75% of the second fastening wing 10, as seen from the front edge 7 and towards the rear edge 8 of the sanitary article 1. The sum of the first and the second wing maximum widths $w_{f1max}+w_{f2max}$ is greater than a width $w_e$ of the absorbent core 4 as measured at the sanitary article transverse centerline $C_T$, however due to the asymmetry of the fastening wings, the fastening wings may be folded narrowly about the longitudinal edges 5, 6 of the sanitary articles 1 in a non-overlapping configuration.

The first fastening wing 9 comprises a first adhesive region 12 on a garment facing side thereof and the second fastening wing 10 comprises a second adhesive region 13 on a garment facing side thereof. The first adhesive region 12 has a first adhesive region maximum width $w_{a1max}$ and the second adhesive regions 13 has a second adhesive region maximum width $w_{a2max}$, the adhesive region maximum widths $w_{a1max}$, $w_{a2max}$ being measured at the widest section of the respective adhesive region 12, 13, as seen in the transverse direction T. The first adhesive region 12 and the second adhesive region 13 each has a non-rectangular shape, with a respective zone with a greater width and a respective zone with a smaller width and with a sloping zone linking the zone with a greater width and the zone with a smaller width.

The first adhesive region 12 has a length $l_{r1}$ and the second adhesive region has a length $l_{r2}$.

Figure 2:
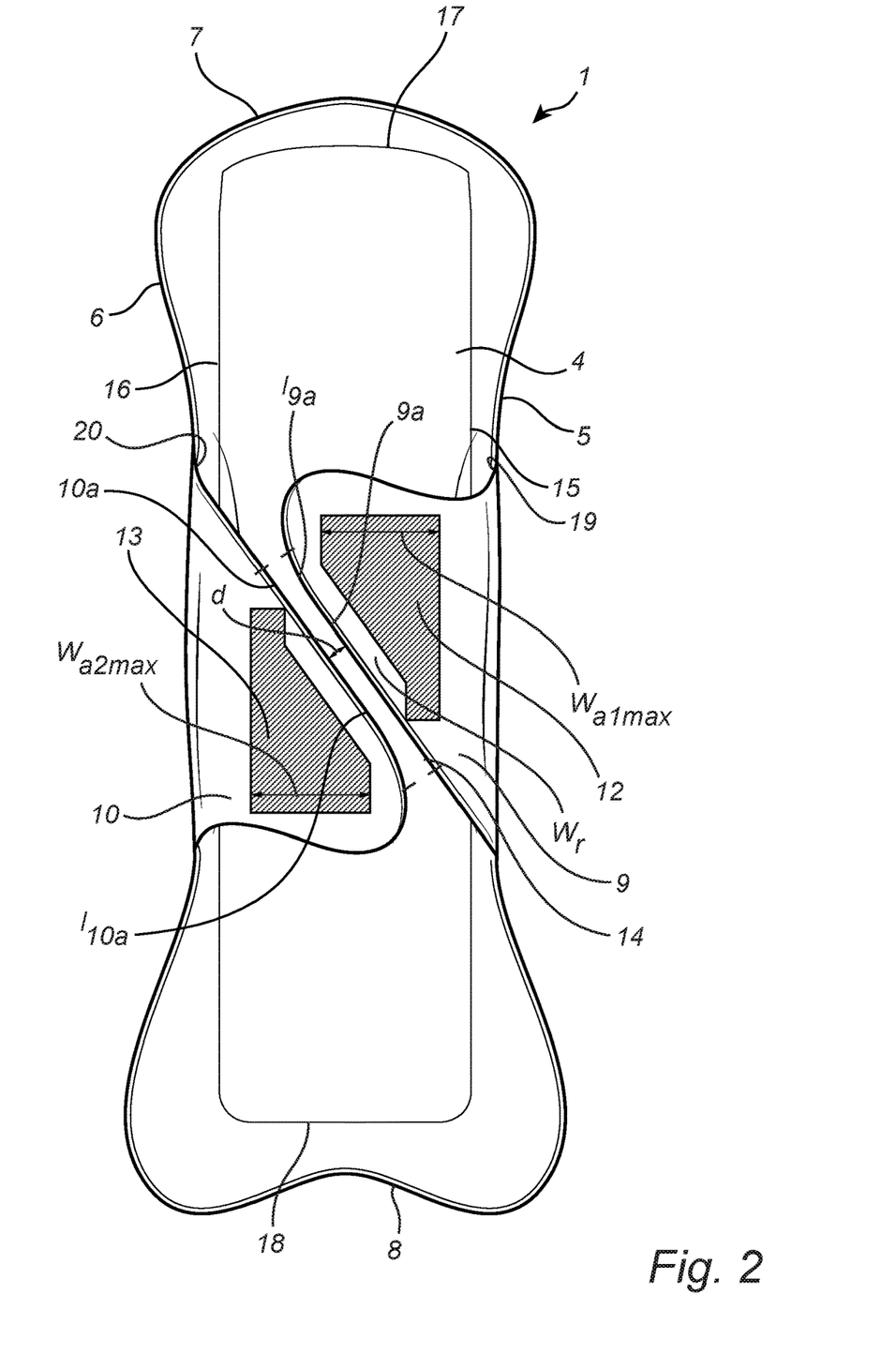
FIG. 2 illustrates the sanitary article from FIG. 1 in a folded configuration, prior to applying the common release paper according to the present disclosure.

In FIG. 2, the sanitary article is arranged in a folded configuration according to the present disclosure with the first and the second fastening wings 9, 10 being folded on top of the topsheet 2 in a non-overlapping manner. The first fastening wing 9 is folded over a first longitudinal fold line 19 and the second fastening wing 10 is folded over a second longitudinal fold line 20. The first and the second longitudinal fold lines 19, 20 are each arranged between 0 and 5 mm from the respective first and longitudinal core side edges 15, 16.

The first fastening wing 9 has a first wing edge section 9a and the second fastening wing 10 has a second fastening wing edge section 10a, the first and second fastening wing edge sections 9a, 10a being arranged opposite and adjacent each other when being folded onto the topsheet 2 of the sanitary article 1. A distance d between the first and the second wing edge sections 9a, 10a is from 0 mm to 10 mm. The first wing edge section 9a and the second wing edge section 10a each has a length $l_{9a}$, $l_{10a}$ of from 15 mm to 80 mm, as measured along a respective edge of the first and second fastening wing 9, 10.

Figure 3:
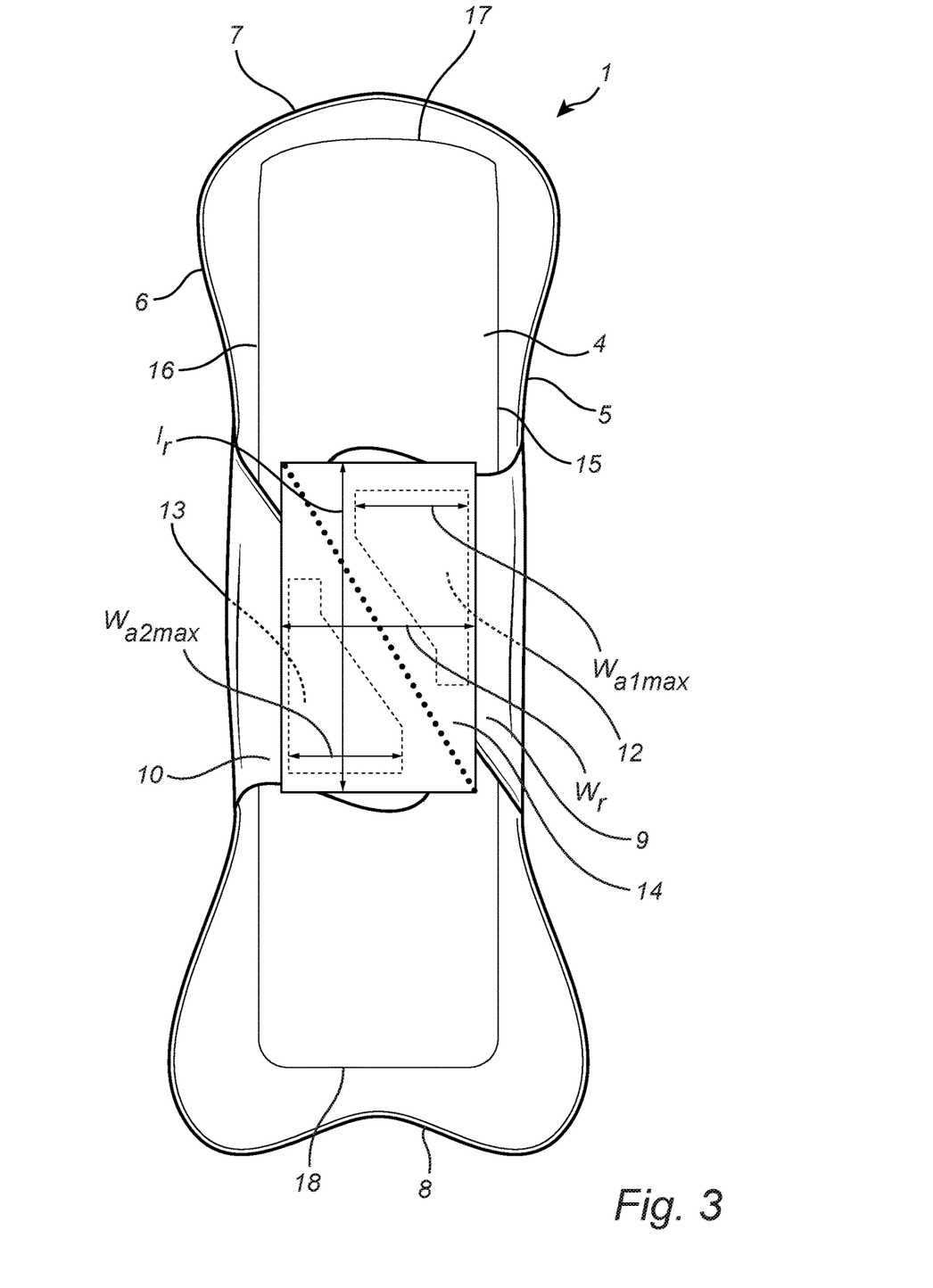
FIG. 3 illustrates a sanitary article provided with a release paper according to an embodiment of the present disclosure.

In FIG. 3, the sanitary article 1 is illustrated with the first and the second adhesive region 12, 13 being covered with a common release paper 14. The common release paper 14 has a width $w_r$, as seen in the transverse direction T, and the width of the release paper $w_r$ is maximum 7 mm greater than the sum of the first and the second adhesive region maximum widths, $w_{a1max}+w_{a2max}$. In this figure, the sum of the first and the second adhesive region maximum widths $w_{a1max}+w_{a2max}$ is greater than that the width of the release paper $w_r$. The release paper 14 has a length $l_r$ extending in the longitudinal direction of the sanitary article 1. The length $l_r$ of the release paper 14 is less than a combined length of the adhesive regions 12, 13 (see FIG. 1).

Figure 4:
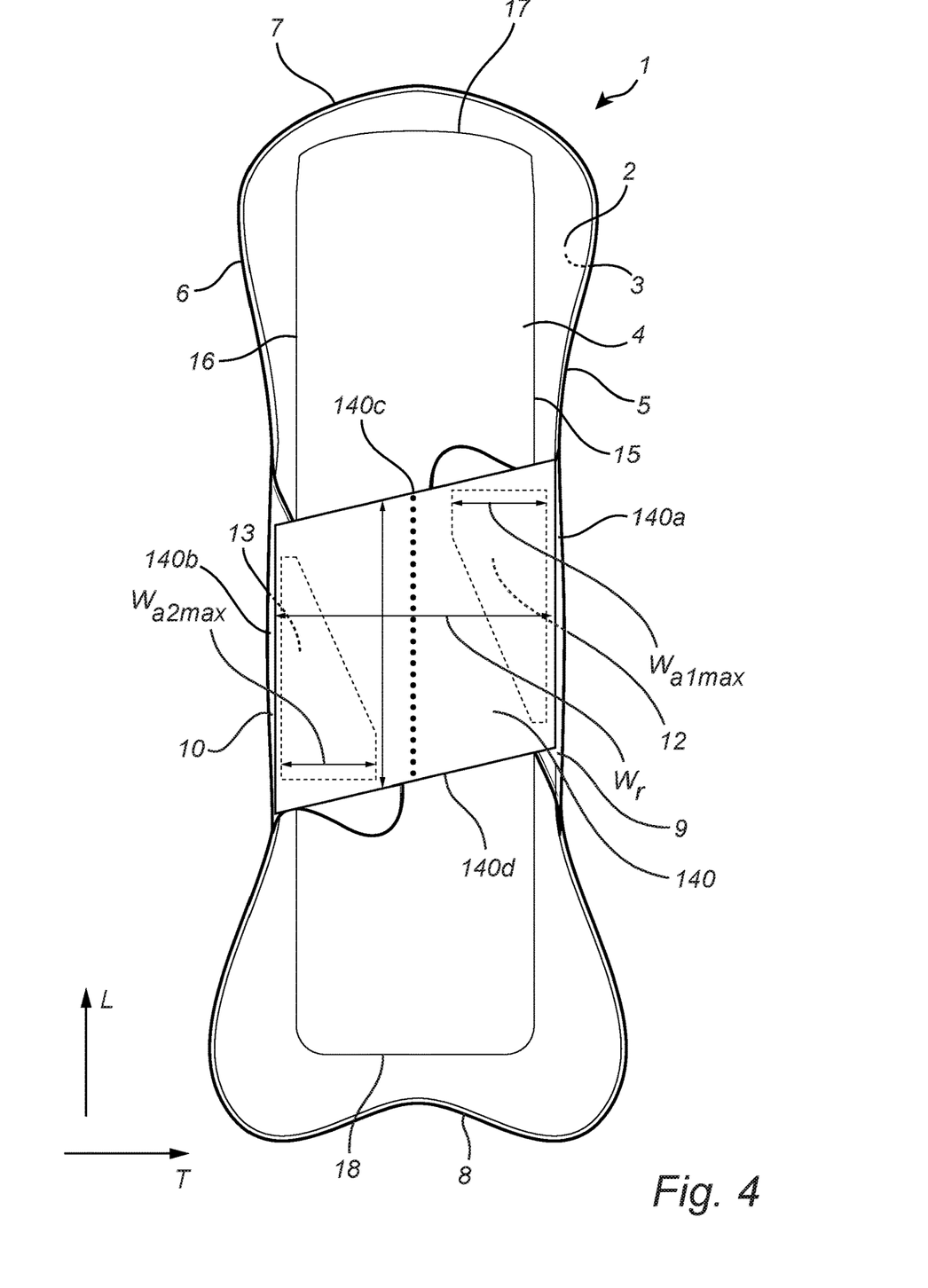
FIG. 4 illustrates a sanitary article provided with a release paper according to a further embodiment of the present disclosure.

FIG. 4 illustrates a sanitary article 1 according to the present disclosure comprising a topsheet 2, a backsheet 3 and an absorbent core 4 arranged between the topsheet 2 and the backsheet 3. The sanitary article 1 extends in a longitudinal direction L and in a transverse direction T.

The sanitary article 1 has a first longitudinal side edge 5 and a second longitudinal side edge 6, a front edge 7 and a rear edge 8. The absorbent core 4 comprises a first longitudinal core side edge 15, a second longitudinal core side edge 16, a front core edge 17 and a rear core edge 18. The sanitary article 1 has a first fastening wing 9 extending outboard at the first longitudinal side edge 5 and a second fastening wing 10 extending outboard at the second longitudinal side edge 6. The first fastening wing 9 comprises a first adhesive region 12 on a garment facing side thereof and the second fastening wing 10 comprises a second adhesive region 13 on a garment facing side thereof. The first adhesive region 12 has a first adhesive region maximum width $w_{a1max}$ and the second adhesive regions 13 has a second adhesive region maximum width $w_{a2max}$, the adhesive region maximum widths $w_{a1max}$, $w_{a2max}$ being measured at the widest section of the respective adhesive region 12, 13, as seen in the transverse direction T. The first adhesive region 12 and the second adhesive region 13 each has a non-rectangular shape, with a respective zone with a greater width and a respective zone with a tapering width. The first and the second adhesive regions 12, 13 are covered with a common release paper 140. The common release paper 140 has a width $w_r$, as seen in the transverse direction T, and the width of the release paper $w_r$ is maximum 7 mm greater than the sum of the first and the second adhesive region maximum widths, $w_{a1max}+w_{a2max}$. In this figure, the sum of the first and the second adhesive region maximum widths $w_{a1max}+w_{a2max}$ is greater than that the width of the release paper $w_r$.

The release paper 140 has the shape of a rhombus. The release paper 140 has a release paper first longitudinal edge 140a, a release paper second longitudinal edge 140b, a release paper first transverse edge 140c and a release paper second transverse edge 140d. The release paper 140 covers the first and second adhesive regions 12, 13 on the first and second fastening wings 9, 10 respectively. The release paper 140 is arranged on the sanitary article 1 such that the release paper first and second longitudinal edges 140a, 140b extend in the longitudinal direction L and such that the release paper first and second transverse edges 140c, 140d are inclined with respect to the transverse direction T.

The invention claimed is:

1. A sanitary article, the sanitary article comprising:
   a topsheet;
   a backsheet;
   an absorbent core arranged between the topsheet and the backsheet; and
   a common release paper,
   wherein the sanitary article extends in a longitudinal direction (L) and in a transverse direction (T),
   wherein the sanitary article has a first and a second longitudinal side edge, a front edge and a rear edge,
   wherein the absorbent core comprises a first longitudinal core side edge, a second longitudinal core side edge, a front core edge and a rear core edge,
   wherein the sanitary article has a first fastening wing extending at the first longitudinal side edge and a second fastening wing extending at the second longitudinal side edge,
   wherein the first fastening wing has a first wing maximum width ($w_{f1max}$) and the second fastening wing has a second wing maximum width ($w_{f2max}$), the first and second wing maximum widths ($w_{f1max}$, $w_{f2max}$) being measured from the respective first and second longitudinal core side edge and at a widest section of the respective fastening wing, as seen in the transverse direction (T),
   wherein the first fastening wing comprises a first adhesive region on a garment facing side thereof,
   wherein the second fastening wing comprises a second adhesive region on a garment facing side thereof,
   wherein the first and the second adhesive regions have a respective adhesive region maximum width ($w_{a1max}$, $w_{a2max}$), the adhesive region maximum widths ($w_{a1max}$, $w_{a2max}$) being measured between transversal edges of the first and the second adhesive regions at a widest section thereof, as seen in the transverse direction (T),
   wherein the common release paper is positioned to simultaneously cover an entirety of both the first adhesive region and the second adhesive region when the first and the second fastening wings are arranged in a folded configuration onto the topsheet in a non-overlapping manner,
   wherein the common release paper has a width ($w_r$), as seen in the transverse direction (T),
   wherein, the first and second fastening wings are asymmetrical with respect to any transverse axis extending in the transverse direction (T) and with respect to each other as seen along any longitudinal axis extending in the longitudinal direction, and
   wherein a sum of the first and the second adhesive region maximum widths ($w_{a1max}+w_{a2max}$) is greater than the width of the release paper ($w_r$).

2. The sanitary article according to claim 1, wherein the sum of the first and the second adhesive region maximum widths ($w_{a1max}+w_{a2max}$) is at least 2 mm greater than that the width of the release paper ($w_r$).

3. The sanitary article according to claim 1, wherein the sum of the first and the second wing maximum widths ($w_{f1max}+w_{f2max}$) is greater than a width ($w_c$) of the absorbent core as measured at a transverse centerline ($C_T$) of the sanitary article.

4. The sanitary article according to claim 1, wherein a width ($w_n$) of the first fastening wing increases over at least 50% of the first fastening wing, as seen from the rear edge and towards the front edge of the sanitary article.

5. The sanitary article according to claim 1, wherein a width ($w_f$) of the second fastening wing increases over at least 50% of the second fastening wing, as seen from the front edge and towards the rear edge of the sanitary article.

6. The sanitary article according to claim 1, wherein the absorbent core is an essentially rectangular core having a width not varying more than ±20 mm along a longitudinal length of the absorbent core.

7. The sanitary article according claim 1, wherein the first and second wings are folded directly at and around the first and second longitudinal core edges.

8. The sanitary article according to claim 1, wherein a length of the release paper ($l_r$) is less than a combined total length ($l_{r1}+l_{r2}$) of the first and the second adhesive regions.

9. The sanitary article according claim 1, wherein the first fastening wing has a first wing edge section and the second fastening wing has a second fastening wing edge section, the first and second fastening wing edge sections being arranged opposite and adjacent each other when being folded onto the topsheet of the sanitary article and a distance (d) between the first wing edge section and the second wing edge section is from 0 mm to 10 mm.

10. The sanitary article according to claim 9, wherein each of the first wing edge section and the second wing edge section has a length ($l_{9a}$, $l_{10a}$) of 10 mm or more as measured along a respective edge of the first and second fastening wing.

11. The sanitary article according to claim 1, wherein at least one of the first adhesive region and the second adhesive regions has a non-rectangular shape.

12. The sanitary article according to claim 1, wherein the first and the second adhesive regions each has a respective portion with a greater width and a respective portion with a smaller width.

13. The sanitary article according to claim 1, wherein the first and the second fastening wing are symmetrically disposed with respect to each other along a diagonal axis extending in a direction (D), in a plane of the sanitary article and with an angle within the range of from 10° to 65° to a longitudinal centerline ($C_L$) of the sanitary article.

14. The sanitary article according to claim 1, wherein the release paper has the shape of a rhombus or a parallelogram, having a release paper first and second longitudinal edges and release paper first and second transverse edges, the release paper being arranged on the sanitary article such that the first and second longitudinal edges extend in the longitudinal direction (L) and the release paper first and second transverse edges are inclined with respect to the transverse direction (D).

15. A sanitary article, the sanitary article comprising:
- a topsheet;
- a backsheet;
- an absorbent core arranged between the topsheet and the backsheet; and
- a common release paper,
- wherein the sanitary article extends in a longitudinal direction (L) and in a transverse direction (T),
- wherein the sanitary article has a first and a second longitudinal side edge, a front edge and a rear edge,
- wherein the absorbent core comprises a first longitudinal core side edge, a second longitudinal core side edge, a front core edge and a rear core edge,
- wherein the sanitary article has a first fastening wing extending at the first longitudinal side edge and a second fastening wing extending at the second longitudinal side edge,
- wherein the first fastening wing having has a first wing maximum width ($w_{f1max}$) and the second fastening wing having has a second wing maximum width ($w_{f2max}$), the first and second wing maximum widths ($w_{f1max}$, $w_{f2max}$) being measured from the respective first and second longitudinal core side edge and at a widest section of the respective fastening wing, as seen in the transverse direction (T),
- wherein the first fastening wing comprises a first adhesive region on a garment facing side thereof,
- wherein the second fastening wing comprises a second adhesive region on a garment facing side thereof,
- wherein the first and the second adhesive regions have a respective adhesive region maximum width ($w_{a1max}$, $w_{a2max}$), the adhesive region maximum widths ($w_{a1max}$, $w_{a2max}$) being measured between transversal edges of the first and the second adhesive regions at a widest section thereof, as seen in the transverse direction (T),
- wherein, when the first and the second fastening wings are arranged in a folded configuration onto the topsheet in a non-overlapping manner, a longitudinal axis extends through at least a portion of the both the first adhesive region and the second adhesive region,
- wherein the common release paper is positioned to cover an entirety of both the first adhesive region and the second adhesive region when the first and the second fastening wings are arranged in a folded configuration onto the topsheet in a non-overlapping manner,
- wherein the common release paper has a width ($w_r$), as seen in the transverse direction (T),
- wherein, the first and second fastening wings are asymmetrical with respect to any transverse axis extending in the transverse direction (T) and with respect to each other as seen along any longitudinal axis extending in the longitudinal direction, and
- wherein a sum of the first and the second adhesive region maximum widths ($w_{a1max}+w_{a2max}$) is greater than the width of the release paper ($w_r$).

* * * * *